United States Patent
Bromberg et al.

(10) Patent No.: US 6,411,673 B1
(45) Date of Patent: Jun. 25, 2002

(54) SAMPLING RATE SCALING OF CALIBRATION VECTORS IN X-RAY CT MACHINES

(75) Inventors: Neil B. Bromberg, Milwaukee; Clarence L. Gordon, III, Delafield, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 4 days.

(21) Appl. No.: 09/751,814

(22) Filed: Dec. 29, 2000

(51) Int. Cl.[7] .................................................. A61B 6/03
(52) U.S. Cl. ............................. 378/19; 378/8; 378/901
(58) Field of Search ........................... 378/4, 8, 15, 19, 378/901

(56) References Cited

U.S. PATENT DOCUMENTS 6,307,912 B1 * 10/2001 He et al. ...................... 378/19

* cited by examiner

*Primary Examiner*—David V. Bruce
(74) *Attorney, Agent, or Firm*—Quarles & Brady LLP

(57) ABSTRACT

Time consuming calibration of a multi-element x-ray detector for an x-ray computed tomography machine that has multi-sample rate capabilities is reduced by determining through the use of air-scans, a scalar relationship between sensitivity of detector elements as a function of sampling rate. This scalar relationship is in vector form and may be applied to independently obtain calibration vectors at a base scan rate to provide effective calibration vectors at a variety of scan rates without the need for time consuming daily calibration scans at each of those sample rates.

15 Claims, 1 Drawing Sheet

SAMPLING RATE SCALING OF CALIBRATION VECTORS IN X-RAY CT MACHINES

BACKGROUND OF THE INVENTION

The present invention relates to x-ray computed tomography machines (CT) and specifically to a method of calibrating CT data when acquired at different sampling rates.

X-ray computed tomography is a well known procedure for creating cross-sectional images from computer processed x-ray projections taken along the plane of the cross section. In a typical CT machine, an x-ray tube is mounted on a rotatable gantry to project the fan beam of x-rays at a patient through a "slice" from a variety of angles. The x-rays are received after passing through the patient by a multi-element detector to provide a measurement of x-ray attenuation along a variety of rays of the fan beam ("projections"). The attenuation signals from the elements of the multi-element detector are sampled and digitized by a data acquisition system.

Digitized projections collected at a range of angles about the patient, typically no less than 180° plus half the fan beam angle, are collected in a "tomographic projection set" and reconstructed according to well known techniques in the art, such as filtered back projection, into an image of a cross section of the patient along that slice.

The mathematics of computed tomography reconstruction require that each detector be extremely stable so that attenuation signals over time are the same when identical x-ray flux is received by those detectors. To realize this stability, the detector elements are manufactured to have similar electrical characteristics and remaining variations are accommodated by means of one or more "correction vectors".

The correction vectors provide a value for each detector element which may be subtracted from or multiplied by corresponding attenuation values ("scan values") acquired by the detectors to correct the attenuation values for detector-to-detector variation. The correction vectors are updated at different intervals. Prior to every scan, an "offset vector" is measured that corrects signal offsets such as from "dark currents" that occur in detectors in the absence of any received x-rays and contains values subtracted from the attenuation values to remove offset. At the time of the scan, a "reference normalize vector" is produced based on a signal received at a reference detector. The vector corrects for variations caused by changes in x-ray tube current.

On a daily basis, an "air calibration vector" is measured which corrects signal scaling from a variety of possible sources including changes in x-ray tube voltage, aperture, focal spot size, filtration and sampling rate. The air calibration vector is measured with nothing in the x-ray beam, prior to scanning patients. Far less frequently, "beam hardening" and "primary speed" correction vectors are measured, the latter which is a function of the detector and does not change for a give detector. These correction vectors are typically measured rarely, once at the time of manufacture and thereafter only at major service intervals, for example, when the x-ray tube or filters are replaced.

Current CT machines allow for selection from a variety of scanning speeds. High scanning speeds may be desired for images where organ or patient movement can be a problem and low signal to noise ratio can be tolerated. Slower scanning speeds are used where motion is less of a problem and high signal to noise ratio images are needed. Each of these scanning speeds may require the use of a different sampling rate of the attenuation signals from the elements of the multi-element detector.

Variations in the sampling rate can significantly affect the air calibration vector. Accordingly, the calibration vector must be measured for each possible sampling rate, significantly increasing the time required to do this daily calibration procedure.

BRIEF SUMMARY OF THE INVENTION

The present inventors have recognized that a simple relationship may be developed between the values of the calibration vectors at different sampling rates. This relationship, which may be determined by executing a series of stationary air-scans at different sampling rates, may be used to modify a limited set of calibration vectors taken at a base sampling rate, for use with any sampling rate.

Generally, the present invention provides a method of calibrating attenuation signals obtained from a multi-element x-ray detector used in an x-ray computed tomography machine where the attenuation signals indicate the strength of x-rays received from an x-ray source after the x-rays pass through a measurement volume. The signals are sampled by a digital acquisition system at different sampling rates. For each of a plurality of different sampling rates including a base rate, the multi-element detector is used to acquire an air-scan vector of signals when the measurement volume is empty of an object to be imaged. The multi-element detector is then used to acquire at a given sampling rate, a tomographic projection set of signals when the measurement volume includes an object to be imaged. A sampling rate correction vector is generated being a function of the air-scan vector for the base rate and the air-scan vector for the given sampling rate and this is used to modify a calibration vector. The modified calibration vector is applied to the tomographic projection set.

DETAILED DESCRIPTION OF THE INVENTION

Figure 1:
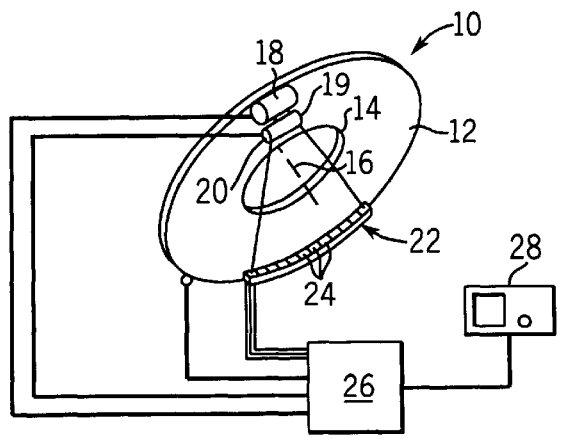
FIG. 1 is a simplified diagram of the principal elements of a commercial tomography machine showing an opposed x-ray source (18) and multi-element detector (22) and a processing system (26) receiving attenuation signals from the multi-element detector and communicating with an operator console.

Referring to FIG. 1, computed tomography machine 10 includes an annular gantry 12 having a central opening 14. The gantry 12 is supported for rotation about an axis 16 centered within the opening 14 and generally perpendicular to a broad face of the gantry 12.

Attached on the face at one edge of the gantry 12 is an x-ray tube 18 directing a fan beam of x-rays 20 across the opening 14 to a multi-element detector 22 attached at an opposite edge of the gantry 12. Elements 24 of the multi-element detector 22 extend along the face of the gantry 12 about a radius centered on the x-ray source. Each element 24 measures attenuation of x-rays 20 caused by an imaged object (not shown) within the opening 14.

A filter/collimator 19 which may include multiple interchangeable filter elements and collimators is placed between the x-ray tube 18 and the opening 14 according to techniques well known in the art.

Attenuation signals from each of the elements 24 is received by a processing system 26 which also controls rotation of the gantry 12, selection of filtration and collimation of the filter/collimator 19 and activation of the x-ray tube 18. A console 28 is also connected to the processing system 26 and provides for input of scanning parameters (e.g., scan speed) from an operator and the output of reconstructed tomographic images to the operator.

Figure 2:
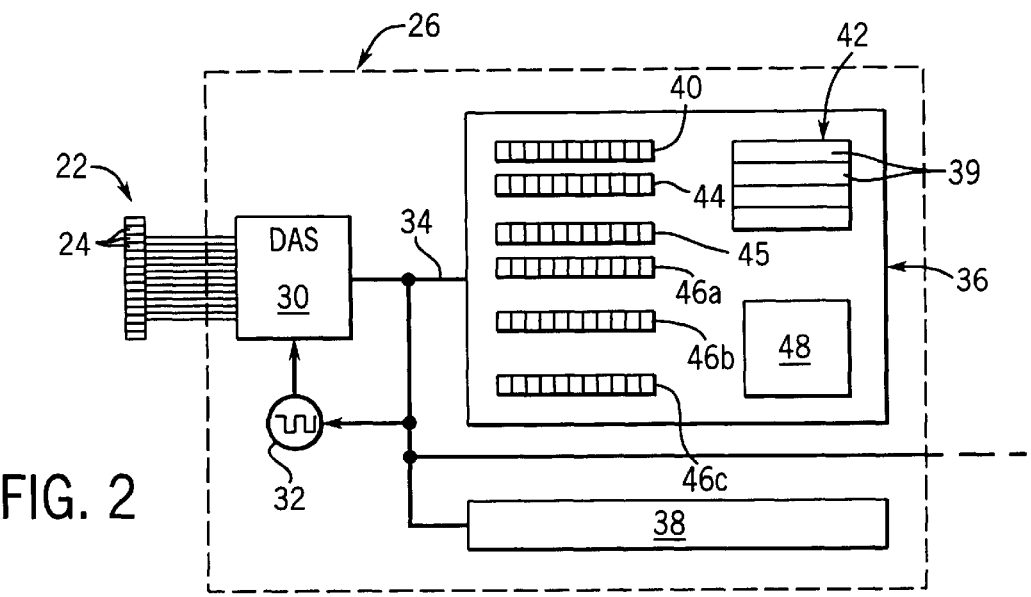
FIG. 2 is a detailed block diagram of the detector (22) and processing system (26) of FIG. 1 showing a data acquisition system (30) such as may acquire data from the multi-element detector at different sampling rates, an associated memory (36) for storing data including air-scan vector ratios (46) and a processor (38) for executing a program (48) to execute the method of the present invention.

Referring now to FIG. 2, detector elements 24 of the multi-element detector 22 each provide independent attenuation signals to a multichannel data acquisition system 30 which samples the independent signals on each of the detector elements 24 at a sampling rate determined by a sample rate clock 32. Generally, the sample rate clock 32 will be adjusted so that the sample rate of the attenuation signals provides a desired angular separation between the projections of an acquired tomographic projection set with different gantry speeds of rotation. As mentioned, the gantry speed may be changed to control the scanning time.

Each of the sampled attenuation signals are digitized and transferred over an internal bus 34 as raw attenuation data. The internal bus 34 also communicating with a memory 36 and processing unit 38. The bus 34 may also communicate via a port (not shown) with the console 28. The processing unit 38 operating through the bus 34 may control the speed of the sample rate clock 32 according the desired scan speed entered by the operator through console 28.

One sampling of the full set of attenuation signals from data elements 24 of the multi-element detector 22 produces a projection vector 39 of values where the vector elements correspond with raw attenuation data of particular detector elements 24. A tomographic projection set 42 will be a set of projection vectors 39 corresponding to different angles of gantry rotation.

Generally, the memory 36 may store a tomographic projection set 42 of vectors for processing as well as a calibration vector 40 and an offset vector 44. The calibration vector 40 includes values that when multiplied by the raw attenuation data of the tomographic projection set (the multiplication being between corresponding elements of the vectors) corrects the raw attenuation data of the projection set 42 for variations in measurements caused by factors other than the attenuation of x-rays so as to reduce artifacts in the reconstructed image. As such, the calibration vector 40 may include calibrations for beam hardening and primary speed, as described above.

The offset vector 44 provides values that when subtracted from the raw attenuation data of the projection set 42 eliminate offsets unrelated to attenuation of x-ray energy. The offset vector 44 is normally applied prior to the calibration vector 40.

Per the present invention, the memory 36 also stores a set of vectors of stationary air-scan ratios 46A through 46C, each related to a different speed of the sample rate clock 32. Vector air-scan ratios 46A through 46C represent multiple attenuation measurement (for each detector element) without gantry rotation and without a patient in the opening 14 of the gantry, taken at different speeds of the sample rate clock 32, averaged and referenced ratiometrically to similarly acquired and averaged attenuation measurements at a reference base sample rate. The measurements at the reference base sample rate form the numerator and the measurements at the different sample rates form the denominators of the air-scan ration 46. The air-scan ratios 46A through 46C provide a measure of interdetector sensitivity differences as a function of different scan rates. The base scanning rate is typically the middle scanning rate.

On a daily basis, air calibrations are done only at the base scanning rate to produce a base scanning rate air scan 45. The air calibration ratios 46 taken earlier can be multiplied by the daily base scanning rate air scan 45 to produce a suitable calibration vector for different sampling rates. While only three different such vectors of stationary air-scan ratios are shown, generally one vector of ratios will be stored for each possible sampling rate however many.

Also included in memory 36 is a program 48 executed by the processing unit 38 to provide machine control and reconstruction as is understood in the art and the calibration process described hereafter being part of the present invention.

Figure 3:
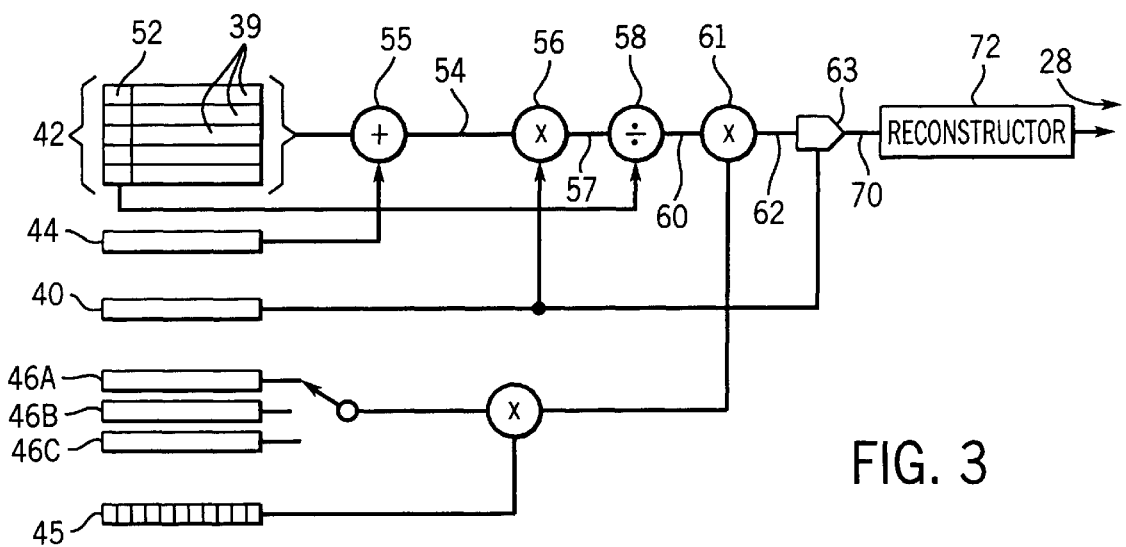
FIG. 3 is a data flow chart showing the reconstructing a projection set (42) using the air-scan ratios (46) of FIG. 2 to create an image.

Referring now to FIG. 3, a projection set 42 of data may be acquired including reference channel data 52 used to generate the reference normalize vector. Each of the projection vectors 39 of the projections set 42 is then corrected by the offset vector 44 which is subtracted from each of the projection vectors 39, the subtraction being performed on an element by element basis to produce offset corrected projections 54 by subtractor 55.

The offset corrected projections 54 are provided to a multiplier 56 to be multiplied by the primary speed correction portion of vector 40. The resulting offset corrected projections 57 are then provided to divider 58 to be divided by a reference normalize vector formed from the reference channel data 52 as is understood in the art. Generally, the reference data 52 for a given projection vector 59 divides the other elements for that projection vector 39.

The thus produced reference corrected data 60 is then provided to multiplier 61 to be multiplied by the product of (1) one of the air-scan ratios 46A–46B as dictated by the sampling rate at which the projection set 42 was acquired and (2) the base scanning rate air scan 45. The thus modified air-scan ratio 46A–46C is applied on an element by element basis by multiplier 61 to produce air scan corrected data 62.

This air scan corrected data 62 is then provided to pre-processor 63 which applies a negative log (reflecting the exponential attenuation of x-rays) and the beam hardening correction of vector 40 according to methods will known in the art. This corrected data 70 is applied to a reconstructor 72 for production of the tomographic image (according to a well known technique) such as is provided to the console 28.

The above described various embodiments of the invention provide for different features. With the invention, the storage space needed for calibration vectors can be reduced and daily acquisitions of air-scans to is limited to a single sampling rate.

It should be noted that the present invention allows for the acquisition of multiple air-scan data vectors for at least one given scan rate and averaging them together and in this way an arbitrary precision may be obtained in the generation of the scaling factor that relates sampling rates to adjustments in the calibration vector.

When the tomography machine may include an x-ray tube mounted in opposition to the multi-element x-ray detector on a rotatable gantry, the air-scans are may be taken without gantry movement, thus a scaling factor can be obtained that isolates the effects of sampling from ancillary effects such as those that may arise with gantry movement.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A method of calibrating attenuation signals from a multi-element x-ray detector used in x-ray computed tomography, the attenuation signals indicating the strength of x-rays received from an x-ray source after passing through a measurement volume, the signals sampled by a digital acquisition system at different sampling rates, the method comprising the steps of:
   (a) for each of a plurality of different sampling rates including a base rate, using the multi-element detector to acquire an air-scan data vector of signals when the measurement volume is empty of an object to be imaged;
   (b) using the multi-element detector to acquire at a given sampling rate, a tomographic projection set of signals when the measurement volume includes an object to be imaged;
   (c) acquire a current air-scan vector for the base rate;
   (d) modify the air scan vector for the given sampling rate by the current air-scan vector for the base rate; and
   (e) apply the modified air scan vector for the given sampling rate to the tomographic projection set;
      whereby a single current air-scan vector for the base rate may be used to derive current air scan vectors at a variety of sampling rates.

2. The method of claim 1 wherein the multi-element x-ray detector is used in an x-ray tomography machine having an x-ray tube mounted in opposition to the multi-element x-ray detector on a rotatable gantry and further having a filtration device moving filters into and out of the x-ray beam and a collimator allowing adjustable collimation of the x-ray beam and wherein the air scan vector for the given sampling rate provides calibrations selected from the group consisting of: calibrations for different voltages applied to the x-ray tube, calibrations for different filters, calibration for different element gain factors, and calibration for different collimations.

3. The method of claim 1 wherein the air scan vector for the given sampling rate modified by multiplying it by a ratio of the current air-scan vector for the base rate divided by an air-scan vector for the base rate acquired at step (a).

4. The method of claim 1 wherein the step of applying the modified air scan vector for the given sampling rate to the tomographic projection set multiplies the elements of the modified air scan vector by corresponding elements of projections of the tomographic projection set.

5. The method of claim 1 including the step of using the multi-element detector to acquire an offset vector where the x-ray source is turned off and subtracting the offset vector from projections of the tomographic projection set prior to step (e).

6. The method of claim 1 wherein step (a) includes the acquisition of multiple air-scan data vectors for at least one given scan rate and averaging together of the multiple air-scan data vectors to one air-scan data vector for the given sampling rate.

7. The method of claim 1 wherein the object to be imaged is a human.

8. The method of claim 1 wherein the base rate is the median frequency sampling rate.

9. The method of claim 1 wherein the tomography machine includes an x-ray tube mounted in opposition to the multi-element x-ray detector on a rotatable gantry and wherein the air-scan data vectors acquired at step (a) are taken without gantry movement.

10. The method of claim 1 further including the step of repetitively acquiring the air-scan at the base rate of step (a) at a first period and repetitively acquiring air-scans at other than the base scan rate at a second period longer than the first period.

11. A calibrator for a multi-element x-ray detector used in x-ray computed tomography, elements of the detectors producing signals indicating the strength of x-rays received from an x-ray source, the x-rays passing through a measurement volume, the calibrator comprising:
   (a) a data acquisition system sampling data from the multi-element x-ray detector at one of a plurality of different sampling rates including a base rate;
   (b) a memory storing:
      (i) multiple air-scan data vector ratios from the multi-element detector taken at different sampling rates including the base rate, with x-rays passing through the measurement volume when empty of an object to be imaged;
      (ii) a air calibration vector for the multi-element x-ray detector;
   (c) an input for receiving a tomographic projection set of signals from x-rays passing through the measurement volume holding an object to be imaged; and
   (d) an arithmetic circuit communicating with the memory to produce a sample rate correction vector being a function of the air-scan vector for the base rate and the air-scan vector for the given sampling rate and to modify the tomographic projection set by the sample rate correction vector and the calibration vector.

12. The calibrator of claim 11 wherein the multi-element x-ray detector is used in an x-ray tomography machine having an x-ray tube mounted in opposition to the multi-element x-ray detector on a rotatable gantry and further having a filtration device moving filters into and out of the x-ray beam and a collimator allowing adjustable collimation of the x-ray beam and wherein the stored calibration vector provides calibrations selected from the group consisting of: calibrations for different voltages applied to the x-ray tube, calibrations for different filters, and calibration for different collimations.

13. The calibrator of claim 11 wherein the memory stores multiple air-scan data vectors for at least one given scan rate and including an averaging circuit averaging together of the multiple air-scan data vectors to one air-scan data vector for the given sampling rate.

14. The calibrator of claim 13 wherein the arithmetic circuit, the averaging circuit and the subtracting circuit are realized as an electronic computer executing a stored program.

15. The calibrator of claim 11 wherein the base rate is the median frequency sampling rate.

* * * * *